US00PP15194P3

(12) United States Plant Patent
Redman

(10) Patent No.: US PP15,194 P2
(45) Date of Patent: Sep. 28, 2004

(54) ***CHRYSANTHEMUM* PLANT NAMED 'MEGA TIME AMBER'**

(50) Latin Name: *Chrysanthemum morifolium*
Varietal Denomination: Mega Time Amber

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 0 days.

(21) Appl. No.: 10/364,285

(22) Filed: Feb. 10, 2003

(65) Prior Publication Data

US 2004/0158906 P1 Aug. 12, 2004

(51) Int. Cl.[7] ..... A01H 5/00
(52) U.S. Cl. ..... Plt./295
(58) Field of Search ..... Plt./295

(56) References Cited

U.S. PATENT DOCUMENTS

PP12,437 P2 3/2002 Noodelijk ..... Plt./296

OTHER PUBLICATIONS

Brummitt, 1997. The Garden, Horticultural Science: Chrysanthemum once again, pp. 662–663.*
1999 Ficor catalog listing Chrysanthemum variety 'Virunga.' See, e.g., p. 4.
2000 Ficor catalog, listing Chrysanthemum varieties 'Virunga' and 'Mega Time.' See, e.g., p. 4.
2001 Ficor catalog, listing Chrysanthemum varieties 'Virunga' and 'Mega Time.' See, e.g., p. 4.
2002 Ficor catalog, listing Chrysanthemum varieties 'Virunga' and 'Mega Time.' See, e.g., p. 4.

* cited by examiner

*Primary Examiner*—Anne Marie Grunberg
*Assistant Examiner*—June Hwu
(74) *Attorney, Agent, or Firm*—Howrey SImon Arnold & White, LLP

(57) ABSTRACT

A new variety of *Chrysanthemum* plant named 'Mega Time Amber,' having a good uniform canopy of amber/golden single flowers and a light green disc producing a dark spot with age. The new variety has a medium tall vigor, free branching, uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Mega Time Amber.'

BACKGROUND OF THE INVENTION

The present invention comprises a new and distinct cultivar of *Chrysanthemum* botanically known as *Chrysanthemum morifolium,* and referred to by the cultivar name 'Mega Time Amber.'

'Mega Time Amber,' identified as 20929-2, originated from a naturally occurring whole plant mutation grown in a controlled planting of the unpatented variety in 'Mega Time' in Chichester, West Sussex, United Kingdom. The new variety 'Mega Time Amber' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Mega Time Amber' is a pot type of *Chrysanthemum* plant variety having amber/golden single flowers and a light green disc producing a dark spot with age.

Comparison with Parent

Plants of the new *Chrysanthemum* variety 'Mega Time Amber' are similar to the parent 'Mega Time' in plant habitat and growth rate. In side-by-side comparisons in Chichester, West Sussex, United Kingdom, under commercial practice, plants of the new *Chrysanthemum* variety 'Mega Time Amber' compared to the plants of the parent 'Mega Time' in the following characteristics.

1. The new variety 'Mega Time Amber' produces amber/golden flowers whereas the parent 'Mega Time' produces light pink flowers.
2. Plants of the new variety 'Mega Time Amber' have similar inflorescence to the plants of the parent 'Mega Time.'

Comparison with Other Varieties

Plants of the new *Chrysanthemum* variety 'Mega Time Amber' are similar to (U.S. Plant Pat. No. 12,437) 'Virunga' in plant habit and growth rate. However in side-by-side comparisons in Chichester, West Sussex, United Kingdom, under commercial practice, plants of the new *Chrysanthemum* variety 'Mega Time Amber' differed from plants of 'Virunga' in the following characteristics.

1. The new variety 'Mega Time Amber' produces golden yellow single flowers whereas 'Virunga' produces orange flowers.
2. Plants of the new variety 'Mega Time Amber' have larger and taller inflorescence than plants of 'Virunga.'

BRIEF DESCRIPTION OF ILLUSTRATION

Typical specimens of the plant and flowers for the new *Chrysanthemum* variety 'Mega Time Amber' are shown in the accompanying digital photograph. The colors shown are as true as possible within the usual limits of this kind of illustration.

FIG. 1 is a whole plant view of the new variety 'Mega Time Amber' grown in a pot. The plant shown in the illustration is 54 days from the commencement of Short Days.

DETAILED BOTANICAL DESCRIPTION

The following description of the new *Chrysanthemum* variety 'Mega Time Amber' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 21 days with a response time of about 7.5 weeks. The new variety is suitable for growth in a temperature range of 15° C. to 25° C.

The new variety may be produced as a spray. The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height: 24 cm.
Width: 35 cm.
Branching characteristics: Upright and free branching.
Lateral branches:
- *Length.*—19 cm.
- *Diameter.*—0.8 cm.
- *Surface texture.*—Slightly pubescent.

Number of breaks from pinch: 5.
Stem:
- *Color.*—137B.
- *Diameter.*—0.5 cm.

Response time: 51 days.
Vigor: Medium/Tall.
Shelf life: 21 days.
Disease/pest (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
- *Type.*—Vegetative propagation via stem cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 12.
Compound or single: Single.
Arrangement of leaves: Alternate.
- *Shape of leaf.*—Typically 5 lobed ovate.
- *Size of leaf.*—Width (cm): 4 Length (cm): 6.
- *Leaf apex.*—Acute.
- *Base.*—Obtuse.
- *Attachment.*—Petioled.
- *Aspect.*—Slight undulating.
- *Margin.*—Palmately lobed.
- *Surface characteristics.*—Top: slightly pubescent. Bottom: pubescent.

Petiole:
- *Color.*—137D.
- *Length.*—1.5 cm.
- *Diameter.*—0.2 cm.
- *Surface texture.*—Slightly pubescent.

Venation: Net prominent mid vein at underside.
- *Color.*—Upper side: near 137C. Under side: near 138B.

Color:
- *Mature leaf, upper side.*—Near 137B; under side: near 138A.
- *Young leaf, upper side.*—Near 137A; under side: near 137D.

Flower

Flower appearance: Matte.
Flower type: Single.
Flower form: Slightly cupped.
Flower shape: Round.
Flowering habit: Cyme.
Number of blossoms per branch: 6.
Inflorescence form: Cyme.
- *Depth of fully expanded blossoms.*—2 cm.
- *Diameter of fully expanded blossoms.*—7 cm.

Phyllaries:
- *Number.*—20.
- *Color.*—Near 137C.
- *Length.*—0.7 to 1.2 cm.
- *Width.*—0.1 to 0.3 cm.
- *Texture/appearance.*—Pubescent.

Peduncle: Peduncle length is shortest at the terminal flower and progressively longer moving down the stem.
- *Length.*—12 cm (average).
- *Diameter.*—0.5 cm.
- *Color.*—Near 137C.
- *Surface.*—Pubescent.
- *Habit.*—Slightly curving.
- *Strength.*—Moderately strong.

Pedicel:
- *Length.*—Terminal: 3 cm; lateral: 4.5 cm.
- *Diameter.*—0.2 cm.
- *Color.*—Near 137C.
- *Surface.*—Pubescent.
- *Habit.*—Slightly curving.
- *Strength.*—Moderately strong.

Ray florets:
*Form/shape.*—Straight with parallel edges and rounded apex.
*Texture/appearance.*—Matte.
*Number per flower.*—25.
*Length.*—3.5 cm; Width: 1 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—120.
*Length.*—0.6 cm; Width: 0.1 cm.
*Diameter of disc.*—1.3 cm.
Fragrance: None.
Flower bud (at onset of color):
*Length.*—1 cm.
*Diameter.*—1 cm.
*Form/shape.*—Spherical.
General flower color:
1. *Ray florets, upper side.*—15B. Immature: near 15A. Mature: near 15B. Older/Fading: near 15C.
2. *Ray florets, under side.*—15B. Immature: near 15A. Mature: near 15B. Older/Fading: near 15C.
3. *Disc florets.*—Immature: near 152C. Mature: near 15C. Older/Fading: near 174B. Dark spot on center of disc: 171A.
4. *Bud.*—15B.

Flower progression with age: Flower form and color does not change with age, however, light green disc darkens with age.
Lastingness of bloom is about 21 days.

Reproductive Organs

Gynoecium present on Ray and Disc florets.

Ray florets per individual flower:
*Pistil number.*—25.
*Stigma color.*—Near 154A.
*Stigma shape.*—Forked.
*Style color.*—Near 154B.
*Style length.*—0.3 cm.
Disc florets per individual flower:
*Pistil number.*—120.
*Stigma color.*—Near 154A.
*Stigma shape.*—Forked.
*Style color.*—Near 154B.
*Style length.*—0.3 cm.

Androecium not observed.

Fruit and seeds: None observed.

What is claimed is:

1. A new and distinct variety of *Chrysanthemum* plant, substantially as described and illustrated herein.

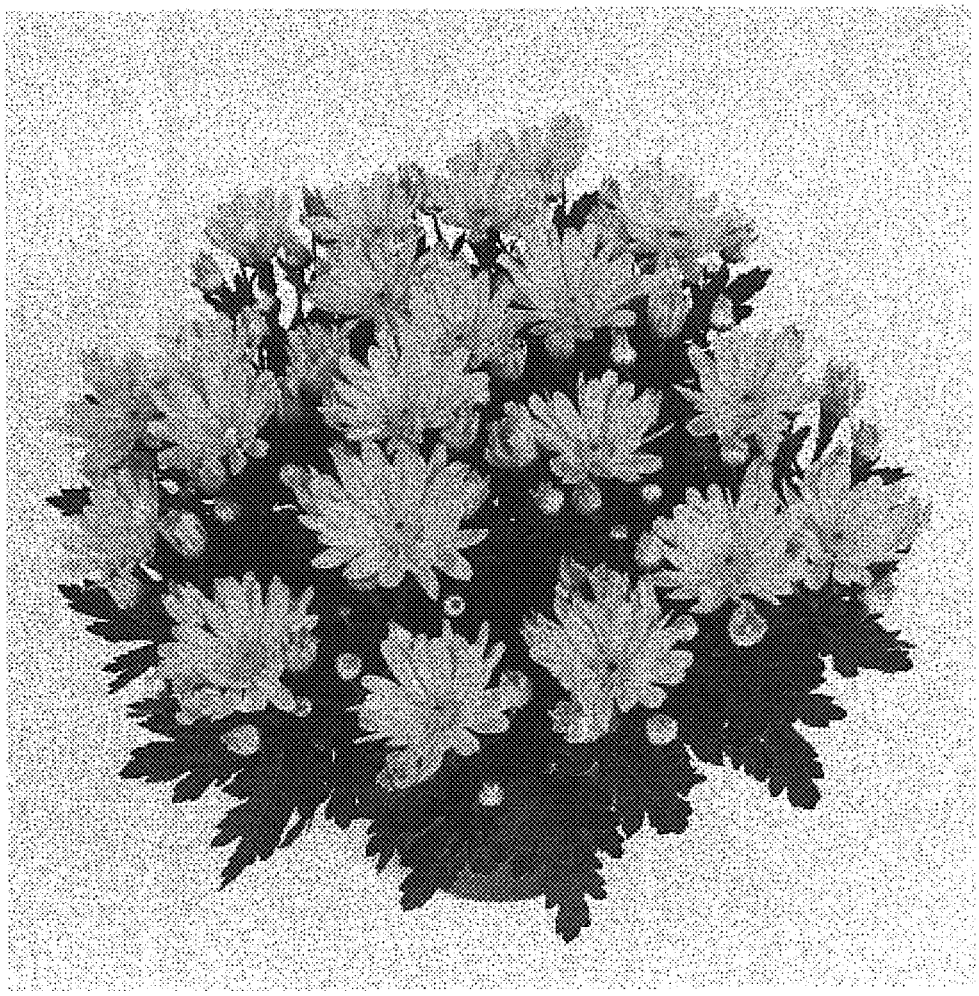

* * * * *